United States Patent [19]

Miyake et al.

[11] 4,442,209

[45] Apr. 10, 1984

[54] PROCESS FOR THE PRODUCTION OF MONASCUS-PIGMENT

[75] Inventors: Toshio Miyake; Shoichi Ohno; Shuzo Sakai, all of Okayama, Japan

[73] Assignee: Kabushiki Kaisha Hayashibara Seibutsu Kagaku Kenkyujo, Okayama, Japan

[21] Appl. No.: 374,685

[22] Filed: May 4, 1982

[30] Foreign Application Priority Data

May 16, 1981 [JP] Japan .................................. 56-73832

[51] Int. Cl.$^3$ .......................... C12P 17/18; C12P 1/02
[52] U.S. Cl. ...................................... 435/119; 435/171
[58] Field of Search ................................ 435/119, 171

[56] References Cited

U.S. PATENT DOCUMENTS 3,765,906 10/1973 Yamaguchi et al. ................. 435/119

Primary Examiner—Alvin E. Tanenholtz
Attorney, Agent, or Firm—Browdy and Neimark

[57] ABSTRACT

A process for the production of Monascus-pigment comprises cultivating, in a nutrient medium containing maltitol, a microorganism of genus Monascus capable of producing said pigment; and harvesting the resultant pigment from the culture.

The process advantageously leads to an extremely higher Monascus-pigment production in comparison with that obtained by conventional process, and, therefore, provides a sufficient amount of the pigment to food industry, where demand for naturally-occurring coloring agent with a high degree of safety is increasing.

6 Claims, No Drawings

PROCESS FOR THE PRODUCTION OF MONASCUS-PIGMENT

FIELD OF INVENTION

The present invention relates to a process for the production of Monascus-pigment.

BACKGROUND

Monascus-pigment is a naturally-occurring red edible pigment, produced by a microorganism of genus Monascus, which has been widely used since antiquity in China and East-South Asian countries in various foodstuffs, e.g., An-chiu and Tou-Fu-Ju.

Recent increasing concern on the use of edible colouring agents has banned various synthetic colouring agents which have a potential of carcinogenicity and/or teratogenicity. This circumstance has inevitably increased demands for highly-safe, naturally-occurring edible colouring agents, one of which is Monascus-pigment.

Some previous studies on the Monascus-pigment production have been reported: for example, *J. Ferment. Technol.*, Vol. 51, No. 6, pp. 407–414 (1973), and *Agr. Biol. Chem.*, Vol. 39, No. 9, pp. 1789–1795 (1975).

Also, some processes for the Monascus-pigment production have been disclosed in Japan Kokai No. 4/80 which describes that the use of a microorganism of genus Monascus with a possible low amylase-producing capability is preferable; and in Japan Patent Publication No. 44,880/73 which describes that desirable constituents for culture medium are saccharides, e.g., glucose and dextrin, and water-soluble proteins.

All attempts disclosed in the patent applications, however, proved unsatisfactorily from point of view of Monascus-pigment yields.

SUMMARY OF INVENTION

The present inventors have investigated various constituents optimal for culture medium, mainly sugar alcohols, in order to establish a process for the industrial-scale production of Monascus-pigment.

The efforts resulted in the unexpected finding that a large amount of Monascus-pigment is easily obtainable by cultivation, in a nutrient medium containing maltitol, a microorganism of genus Monascus capable of producing said pigment, which led to the present invention.

More particularly, the invention relates to an improved process for the production of Monascus-pigment, characterized by cultivating in a nutrient medium containing maltitol a microorganism of genus Monascus capable of producing said pigment, and harvesting the resultant pigment from the culture.

DETAILED DESCRIPTION OF EMBODIMENTS

As to the microorganisms of genus Monascus usable in the invention, any microorganisms can be used so far as they produce Monascus-pigment in the course of their cultivation: preferable species are, for example, *Monascus anka* ATCC 16360, *Monascus anka* IFO 6540, and *Monascus purpreus* IFO 4513.

Usable culture media for the cultivation are those containing maltitol, on which said microorganism can grow and release the pigment. Also, dependent upon the cultivation methods employed, the maltitol content in the culture media falls in the range from about 0.1 to 95% on dry solid basis, preferably from about 1 to 90% on dry solid basis.

Usually, to the culture media may be added other substance(s), e.g., minerals such as phosphate, sulfate, sodium salts, potassium salts, magnesium salts, calcium salts or iron salts; and there may be added further, if necessary, starch or amylaceous substance, such as grain or tuber, wherein starch is the predominant constituent, as carbon source; organic or inorganic nitrogen compounds such as nitrate, ammonium salts, protein, peptide or amino acid, as nitrogen source; and a small amount of ethanol solution of Monascus-pigment as an inducer.

It has been also found that the combination of maltitol with magnesium-L-asparatate and/or amylaceous substance gives a remarkable synergic effect on the production of Monascus-pigment.

The cultivation methods employable in the invention are submerged- and solid culture methods, wherein a microorganism of genus Monascus capable of producing the pigment is usually cultivated at a temperature in the range from 25° to 40° C. for about 2–15 days.

As to the method for the collection of the pigment from the culture, any methods can be employed in the invention without any consideration so long as the pigment can be harvested from the culture by such method, and the resultant pigment is usable in foodstuffs: For example, in the case of solid culture, the culture may be dried and pulverized without further processings to obtain a powder product, or, alternatively, the powder product may be further subjected to extraction step using organic solvent, e.g., ethanol, to obtain a liquid product. Evaporation and removal of the solvent from the liquid product gives a Monascus-pigment with a high purity in the form of paste or powder.

In the case of submerged culture, the culture may be used intact as an edible colouring agent in liquid form for foodstuff processings, or, usually, flocculated by adding thereto a flocculant, e.g., alum, and the resultant product is separated into a liquid part and an insoluble part containing mycelia by means of centrifugation and/or filtration. Since a large amount of the pigment is present in the mycelia, the insoluble part may be subjected similarly as in the case of solid culture to further extraction using organic solvent.

The Monascus-pigment thus obtained is favourably usable as a naturally-occurring red edible colouring agent for colouring various foodstuffs, e.g., confectioneries, candles, frozen-desserts, milk products, meat products, fish-meat products, soft drinks, yogurt drinks, noodles, daily products, canned foods, bottled foods and pickles.

The following EXPERIMENTs concretely explain the present invention.

EXPERIMENT 1

Screening of the carbon source

Screening of carbon source used in the cultivation of the microorganism of genus Monascus to produce Monascus-pigment was carried out mainly with sugar alcohols.

The seed culture was carried out as follows: Five hundred-ml shake flasks, containing 50 ml aliquots of a medium (pH 6.2) consisting of 5.0 w/v % rice powder, 0.25 w/v % $KH_2PO_4$, 0.15 w/v % $NaNO_3$, 0.1 w/v % $MgSO_4.7H_2O$, 0.1 w/v % casamino acid, 0.001 w/v % $CaCl_2.2H_2O$ and tap water, were autoclaved at 120° C.

for 20 minutes to effect sterilization, cooled, and inoculated with *Monascus anka* ATCC 16360, in usual way. Thereafter, the mixtures were cultivated therein at 30° C. for four days under shaking conditions.

Then, the main culture was carried out as follows: Five hundred-ml shake flasks, containing 50 ml aliquots of a medium consisting of 3 w/v % of one variety of the substances listed in TABLE 1 (all percentages are expressed on dry solid basis), as carbon source, 0.25 w/v % $KH_2PO_4$, 0.20 w/v % $NaNO_3$, 0.1 w/v % $MgSO_4.7H_2O$, 0.1 w/v % casamino acid, 0.001 w/v % $CaCl_2.2H_2O$ and tap water, were autoclaved at 120° C. to effect sterilization, cooled, and inoculated with the seed culture in respective inocula of 2 v/v %, similarly as in the above. The, the mixtures were cultivated therein at 30° C. for 7 days under shaking conditions.

The experimental results are given in TABLE 1, wherein the Monascus-pigment production ($A_{500}$) was determined as follows: After adjusting 50 ml of the culture medium to pH 6.5 by the addition of 3N hydrochloric acid and/or sodium hydroxide, the culture medium was placed in a 500-ml Erlenmyer flask, and then added with 200 ml anhydrous ethanol to give an 80 v/v % ethanol solution. Thereafter, the flask containing the solution was placed on a rotary shaker at 30° C. for one hour to effect extraction of the pigment, and the resultant extract was filtrated with a commercially-available filter paper, "Toyo Roshi No. 2", Toyo Roshi Company, Limited, Tokyo, Japan. The resultant filtrate was then, if necessary, diluted with an 80 v/v % aqueous ethanol solution. After the dilution, the absorbance of the filtrate was determined at the wave length of 500 nm using 1 cm cell, and the pigment production was estimated by using the following equation:

$$\text{Production of Monascus-pigment}(A_{500}) = \text{Absorbance} \times \frac{250}{50} \times \text{Dilution}$$

As obvious from the experimental results as shown in TABLE 1, maltitol is the most desirable carbon source among those tested in the pigment production.

TABLE 1

| No. | Carbon source (3.0 w/v %) | Pigment production ($A_{500}$) |
|---|---|---|
| 1 | Ethanol | 7.1 |
| 2 | Glucose | 0.8 |
| 3 | Maltose | 3.2 |
| 4 | Soluble starch | 1.7 |
| 5 | Rice powder | 3.7 |
| 6 | Xylitol | 4.1 |
| 7 | Mannitol | 0.4 |
| 8 | Sorbitol | 2.8 |
| 9 | Dulcitol | 4.2 |
| 10 | Maltitol | 31.4 |
| 11 | Hydrogenated maltose syrup* | 29.5 |
| 12 | Isomaltitol | 3.9 |
| 13 | Lactitol | 3.1 |
| 14 | Cellobiitol | 2.9 |
| 15 | Maltotriitol | 4.4 |
| 16 | Maltotetraitol | 3.8 |
| 17 | Amylitol | 2.9 |

Note:
Hydrogenated maltose syrup* was a commercially-available product with a maltitol content of about 78% on dry solid basis, "MABIT", Registered Trade Mark of Hayashibara Company, Limited, Okayama, Japan.

EXPERIMENT 2

Screening of the nitrogen source

Substances, mainly amino acids, were screened with a purpose to determine optimal nitrogen source in a nutrient medium containing maltitol as carbon source.

Cultivation was carried out similarly as in EXPERIMENT 1 to produce Monascus-pigment, except that the maltitol content in the culture media was 3.0 w/v %, and the content of casamino acid was 0.5 w/v % as in TABLE 2.

The experimental results are given in TABLE 2.

TABLE 2

| No. | Nitrogen source (0.5 w/v %) | Pigment production ($A_{500}$) |
|---|---|---|
| 1 | No | 28.8 |
| 2 | Casamino acid | 36.6 |
| 3 | Yeast extract | 30.3 |
| 4 | Polypeptone | 38.3 |
| 5 | Glycine | 32.5 |
| 6 | L-Alanine | 43.1 |
| 7 | L-Glutamic acid | 44.7 |
| 8 | Sodium-L-glutamate | 47.2 |
| 9 | Magnesium-L-glutamate | 45.0 |
| 10 | L-Asparagine | 58.6 |
| 11 | L-Aspartic acid | 62.5 |
| 12 | Sodium-L-asparatate | 62.1 |
| 13 | Potassium-L-asparatate | 66.2 |
| 14 | Magnesium-L-asparatate | 116.4 |

As obvious from the experimental results as shown in TABLE 2, among the nitrogen sources as tested, combination of maltitol with L-asparagine, L-aspartic acid, or L-asparatate, especially, magnesium-L-asparatate, gives the highest Monascus-pigment production.

EXPERIMENT 3

Combination of maltitol with magnesium-L-asparatate and rice powder

Synergic effect on the pigment production was investigated by using maltitol and magnesium-L-asparatate, both confirmed by EXPERIMENTs 1 and 2 as excellent constituents for culture medium, in combination with powder of old rice: To a fundamental medium, consisting of 0.25 w/v % $KH_2PO_4$, 0.2 w/v % $NaNO_3$, 0.1 w/v % $MgSO_4.7H_2O$, 0.001 w/v % $CaCl_2.2H_2O$ and tap water, was added 3.0 w/v % maltitol, 0.5 w/v % magnesium-L-asparatate and/or 3.0 w/v % rice powder to prepare the nutrient culture medium in TABLE 3. Thereafter, the main cultivation was carried out similarly as in EXPERIMENT 1 to produce the pigment. The pigment production was estimated similarly as in the same EXPERIMENT, and the results are given in TABLE 3.

TABLE 3

| No. | Medium formulation | Pigment production ($A_{500}$) |
|---|---|---|
| 1 | Fundamental medium | 0.1 |
| 2 | Fundamental medium plus maltitol | 28.8 |
| 3 | Fundamental medium plus AspMg | 15.1 |
| 4 | Fundamental medium plus rice powder | 2.6 |
| 5 | Fundamental medium plus maltitol plus AspMg | 116.4 |
| 6 | Fundamental medium plus maltitol plus rice powder | 107.3 |
| 7 | Fundamental medium plus AspMg plus rice powder | 41.4 |
| 8 | Fundamental medium plus maltitol plus AspMg plus | 243.0 |

TABLE 3-continued

| No. | Medium formulation | Pigment production ($A_{500}$) |
|---|---|---|
| | rice powder | |

Note:
AspMg is the abbreviation of magnesium-L-asparatate.

As obvious from the experimental results as shown in TABLE 3, the combination of maltitol with magnesium-L-asparatate and rice powder does give a remarkable synergic effect on the production of Monascus-pigment.

Several embodiments of the invention are disclosed hereinafter.

EXAMPLE 1

Sixteen liters of a medium, consisting of 5 w/v % maltitol, 0.7 w/v % magnesium-L-asparatate, 0.25 w/v % $KH_2PO_4$, 0.2 w/v % $NaNO_3$, 0.1 w/v % $MgSO_4.7H_2O$, 0.001 w/v % $CaCl_2.2H_2O$ and tap water, was placed in a 30-liter jar fermentor, and autoclaved therein at 120° C. for 30 minutes to effect sterilization. After cooling, the medium was inoculated with a seed culture of *Monascus anka* ATCC 16360 in an inoculum of 2 v/v %, and the mixture was cultivated therein at 33° C. for 4 days in usual way under aeration and agitation conditions to obtain a deep orange-coloured culture.

The Monascus-pigment production in the culture was determined similarly as in EXPERIMENT 1 using 50 ml of the culture. The pigment production was about 172.3.

The Monascus-pigment thus obtained is favourably usable as a red colouring agent for colouring various foodstuffs with high protein content, e.g., fish-meat products, meat products and artificial-meat products.

EXAMPLE 2

Sixteen liters of a medium, consisting of 4.0 w/v % hydrogenated maltose syrup, "MABIT", Registered Trade Mark of Hayashibara Company, Limited, Okayama, Japan, 0.5 w/v % magnesium-L-asparatate, 3.0 w/v % rice powder, 0.25 w/v % $KH_2PO_4$, 0.15 w/v % $NaNO_3$, 0.1 w/v % $MgSO_4.7H_2O$ and tap water, was placed in a 30-liter jar fermentor, and the medium was autoclaved therein at 120° C. for 30 minutes to effect sterilization. After cooling, to the medium was added 300 ml of a Monascus-pigment ethanol solution, containing the pigment in an amount giving an absorbance of about 2.0 under the hereinbefore defined conditions, and the mixture was then inoculated similarly as in EXAMPLE 1 with a seed culture of *Monascus anka* ATCC 16360, followed by a six-day cultivation at 30° C. under aeration and agitation conditions, obtaining a deep orange-coloured culture.

The pigment production in the culture was determined similarly as in EXPERIMENT 1. The Monascus-pigment production was about 246.2.

Thereafter, to the culture was added 4 w/v % alum solution, and the mixture was adjusted to pH 6.5 with 5 N sodium hydroxide, followed by centrifugation of the resultant, obtaining a sediment with a high Monascus-pigment content.

The sediment was then subjected to extraction in two volumes of anhydrous ethanol at 60° C. for two hours, and the residue was subjected twice to similar extraction to obtain a deep red-purple-coloured ethanol solution with a high Monascus-pigment content.

The yield was about 90% against the starting culture.

The ethanol solution with a high Monascus-pigment content is favourably usable as a red colouring agent for colouring various foodstuffs, e.g., alcoholic drinks such as wine and liquor; confectioneries such as jelly, bavaroise and candy; soft drinks such as juice and carbonated drinks; and frozen-desserts such as sherbet and ice-cream, as well as for colouring pickles, e.g., "FUKUZIN-ZUKE"-a type of Japanese-style pickles.

EXAMPLE 3

One kg of polished rice was washed with water, and soaked for two hours in 3 liters of a hydrogenated maltose syrup, "MABIT", Registered Trade Mark of Hayashibara Company, Limited, Okayama, Japan, in a concentration of 1% on dry solid basis. After draining off the water for one hour, the rice was placed in a vessel, called "KOJI-BUTA" and equipped with metal mesh at its bottom, and autoclaved therein at 120° C. for 30 minutes to effect sterilization. After cooling under ambient conditions, the content was inoculated with *Monascus anka* IFO 6540 by spraying its seed culture thereto, and then cultivated at 33° C. for 10 days to obtain a red koji. The red koji was heated by hot air, and pulverized to obtain an about 910 g powder product.

In this EXAMPLE, the Monascus-pigment production was determined as follows: Two g of the powder was placed in a 500-ml Erlenmyer flask, and added with 250 ml of an 80 v/v % aqueous ethanol solution. Thereafter, the absorbance of the solution was determined similarly as in EXPERIMENT 1 to estimate the pigment production. The pigment production was about 145.2.

The powder thus obtained is also favourably usable as a red edible colouring agent for colouring various foodstuffs, e.g., seasonings such as tomato puree and catsup; jams such as those from raspberry and strawberry; "KASU-ZUKE" such as that of shellfish-a type of Japanese-style pickled product; and "KOJI-ZUKE" such as those of lobster and sea bream-a type of Japanese-style pickled product. In addition to the above described foodstuffs, the powder product is usable for producing An-chiu.

We claim:

1. In the process for the production of Monascus-pigment which comprises cultivating in a nutrient medium a microorganism of genus Monascus capable of producing said pigment, and harvesting the resultant pigment from the culture, the improvement whereby the production of Monascus-pigment is greatly increased, comprising cultivating said microorganism in a nutrient medium containing 0.1–95% maltitol as a carbon source.

2. A process as set forth in claim 1, wherein the maltitol content in the medium falls in the range from 1 to 90% on dry solid basis.

3. A process as set forth in claim 1, wherein said microorganism is *Monascus anka* ATCC 16360, *Monascus anka* IFO 6540, or *Monascus purpreus* IFO 4513.

4. A process as set forth in claim 1, wherein said microorganism is cultivated in a nutrient medium further containing amylaceous substance, and one or more members selected from the group consisting of L-asparagine, L-asparatic acid, magnesium-L-asparatate, sodium-L-asparatate, and potassium-L-asparatate.

5. A process as set forth in claim 4, wherein said amylaceous substance is rice powder.

6. A process as set forth in claim 1, wherein said microorganism is cultivated in the presence of an ethanol solution of Monascus-pigment to induce the Monascus-pigment production in the microorganism.

* * * * *